(12) United States Patent
Yakis

(10) Patent No.: US 10,010,156 B2
(45) Date of Patent: Jul. 3, 2018

(54) CONTOUR TANNING MASK

(71) Applicant: Valentina Yakis, Gervais, OR (US)

(72) Inventor: Valentina Yakis, Gervais, OR (US)

(*) Notice: Subject to any disclaimer, the term of this patent is extended or adjusted under 35 U.S.C. 154(b) by 394 days.

(21) Appl. No.: 14/959,326

(22) Filed: Dec. 4, 2015

(65) Prior Publication Data

US 2017/0156477 A1 Jun. 8, 2017

(51) Int. Cl.
*A45D 44/12* (2006.01)
*A61N 5/06* (2006.01)
*A41D 13/11* (2006.01)
*A45D 44/00* (2006.01)

(52) U.S. Cl.
CPC .......... *A45D 44/12* (2013.01); *A41D 13/1107* (2013.01); *A61N 5/0614* (2013.01); *A45D 44/002* (2013.01)

(58) Field of Classification Search
CPC ...... A45D 27/42; A45D 44/002; A45D 44/12; A45D 40/0087; A61N 5/0614; A41D 13/11; A41D 13/1107; A41D 13/1146; A41D 13/1161; A42B 3/18; A42B 3/20
USPC ................... 132/319; 2/9, 15; 128/857, 858; 604/303
See application file for complete search history.

(56) References Cited

U.S. PATENT DOCUMENTS

| | | | | |
|---|---|---|---|---|
| 2,124,431 A * | 7/1938 | Praytor | ................. | A45D 44/12 2/174 |
| 4,837,961 A * | 6/1989 | Keenan | ................. | F41C 7/025 42/72 |
| 4,944,312 A * | 7/1990 | Smith | ................ | A41D 13/1161 128/207.11 |
| 5,669,395 A * | 9/1997 | Thompson | ............. | A41D 7/006 128/846 |
| 2003/0028946 A1* | 2/2003 | Zegarelli | ................ | A41D 13/11 2/9 |

* cited by examiner

*Primary Examiner* — Tatiana Nobrega
(74) *Attorney, Agent, or Firm* — Jerry D Haynes; Law Office of Jerry D Haynes

(57) ABSTRACT

A mask for facial contouring that includes: a main portion, where the main portion is adapted to cover a portion of a user's face leaving exposure of a user's outer jaw bone; eye covers, where the eye covers cover the user's eyes; a lip cover, where the lip cover covers the user's lips; temple covers extending from the main portion covering each temple area of the user's face; slit openings along a nose section of the mask; openings at a forehead portion of the mask; and an ear loop on each side of the mask for attaching the mask to the user's face. Each side of the mask may include curved exposure of the user's outer jaw bone and preferably the mask includes a soft material on an interior of the mask.

3 Claims, 1 Drawing Sheet

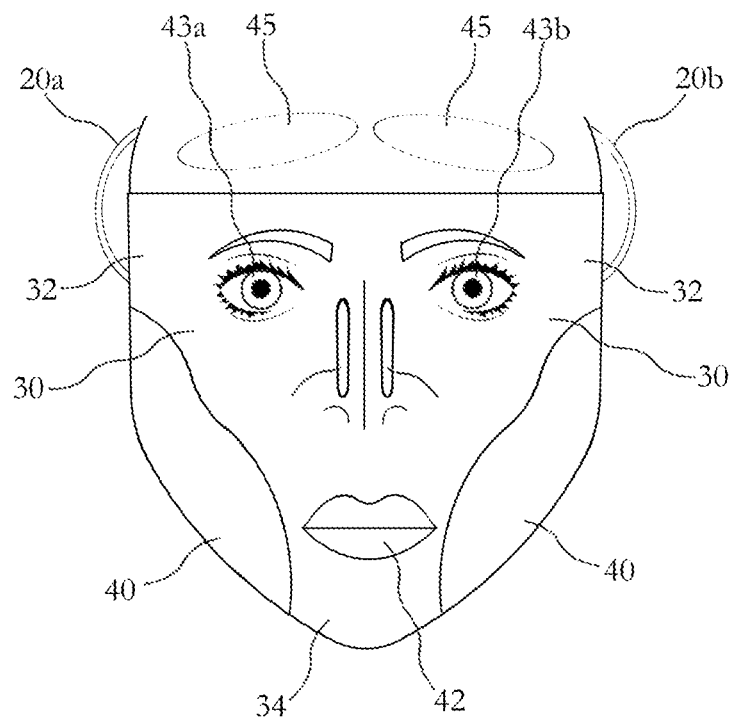

CONTOUR TANNING MASK

BACKGROUND OF THE INVENTION

Field of Invention

The present invention relates to a contour tanning mask that is used for cosmetic purposes.

Description of Related Art

Many women use a tanning bed to help with the cosmetic look of their face. The one particular goal of women who use tanning as a cosmetic feature relates to the contoured face. Many times a woman may place cloth or material on their face in order to limit and focus the tan areas of their face for contouring purposes. This provides the ideal look and allow for the middle of the face to have a lighter shade and the outside of the face to have a darker shade therefore enabling the contouring application of makeup. As a result it will be advantageous to have a mask that is specifically designed for contouring purposes.

SUMMARY OF THE INVENTION

The present invention relates to a mask for facial contouring that includes: a main portion, where the main portion is adapted to cover a portion of a user's face leaving exposure of a user's outer jaw bone; eye covers, where the eye covers cover the user's eyes; a lip cover, where the lip cover covers the user's lips; temple covers extending from the main portion covering each temple area of the user's face; slit openings along a nose section of the mask; openings at a forehead portion of the mask; and an ear loop on each side of the mask for attaching the mask to the user's face. Each side of the mask may include curved exposure of the user's outer jaw bone and preferably the mask includes a soft material on an interior of the mask.

BRIEF DESCRIPTION OF DRAWINGS

FIG. 1 depicts a contouring mask in accordance with the present invention.

DETAILED DESCRIPTION

The present invention relates to a contouring tanning mask. The contour tanning mask according to the present invention covers a great portion of a user's face however it allows for face exposure along the outer jaw lines, forehead and openings provided along the length of the nose. These particular key areas of exposure allow for the increased tanning in these areas and enables a user to create a contour appearance on their face.

In reference to FIG. 1, a contour tanning mask in accordance with the present invention is depicted. The contour tanning mask according to the present invention provides a mask that covers the user's face in critical areas but enables face exposure along the outer jaw bones, above the forehead and slit openings provided along the nose of the mask. A tanning Mask 30 is shown in FIG. 1 which includes slit Openings 46a, 46b along the length of the nose area of the mask. Eye Covers 43a, 43b are shown along with lip Covers 42. Further the Mask 30 extends along the greater portion of the interior surface of the face but leaves facial Exposure 40 on each side of the Mask 30. The outer perimeter of the Mask 30 is somewhat curved downwardly to the chin Cover 34 below the lip Cover 42. Above the eye Covers 43a, 43b and facial exposure is provided at the top of the forehead, Exposure 45. This forehead exposure provides for tanning above the outer portion of the user's forehead. The Mask 30 is contoured for the face exposure at the outer jaw bone along the length of the nose and at the upper forehead of the user. This mask also covers the temple area, Covering 32, extending along the outer temples of the Mask 30. A user attaches this Mask 30 to their face using ear Loops 20a, 20b provided on each side of the contour Mask 30. As a result a user easily may cover their face with this mask while tanning to create a contoured look as desired.

Although not shown but the interior of the mask preferably includes a comfortable soft material, so that it may be placed on the user's face. Once placed on the user's face the silhouette affect may be provided through the tanning process. The outer surface of the mask will be made of a light material capable of use under a tanning bed. The instant invention has been shown and described in what it considers to be the most practical and preferred embodiments. It is recognized, however, that departures may be made there from within the scope of the invention and that obvious modifications will occur to a person skilled in the art.

What is claimed is:

1. A facial mask for contouring the face during tanning or makeup application, comprising:
    an upper edge having opposing right and left end portions, the upper edge is configured to extend horizontally across a user's face between right and left temples;
    a lower edge opposite the upper edge and having opposing right and left end portions, the lower edge is convexly curved and configured to extend along a user's chin;
    a right side edge extending between the right end portions of the upper and lower edges and a left side edge extending between the left end portions of the upper and lower edges, the right and left side edges are curved and taper inwardly from the upper edge toward the lower edge such that the upper edge has a larger dimension than the lower edge and the right and left side edges are configured to expose the user's outer jaw bone;
    right and left ear loops provided on opposing sides of the mask proximate the upper edge, where the first and second ear loops are configured to receive a user's ears for attaching the mask to the user's face;
    the mask defines a longitudinal axis extending through a center thereof between the upper and lower edges, where the mask is symmetrical about the longitudinal axis;
    a first vertical slot disposed in a central portion of the mask to the left of the longitudinal axis and a second vertical slot disposed in a central portion of the mask to the right of the central longitudinal axis, where the first and second vertical slots are configured to extend along left and right side portions of a user's nose, respectively, so that these portions of the nose are exposed;
    wherein during use, the mask is positioned over the face so that the longitudinal axis extends between the eyes and along the bridge of the nose and the mask covers the user's eyebrows, eyes, cheeks, mouth, chin and portions of the nose while exposing the forehead, outer jaw line and portion of the nose corresponding to the first and second vertical slots.

2. The mask for facial contouring according to claim 1, where the mask includes a soft material on an interior surface of the mask.

3. A method of creating a contoured facial tan comprising the steps of:
    a. providing the mask of claim 1;

b. placing the mask over the user's face; and
c. exposing the user's face to tanning rays.

\* \* \* \* \*